United States Patent
Stoycos et al.

(10) Patent No.: US 7,069,071 B2
(45) Date of Patent: *Jun. 27, 2006

(54) DISTRIBUTED MULTI-USER REPLICATION-BASED SYSTEM FOR REAL TIME DATA ACCESS DURING CARDIOLOGY PROCEDURES

(75) Inventors: Stephen T. Stoycos, Sugarland, TX (US); Ewin Michael Kiser, Katy, TX (US)

(73) Assignee: GE Medical Systems, Inc., Waukesha, WI (US)

( * ) Notice: Subject to any disclaimer, the term of this patent is extended or adjusted under 35 U.S.C. 154(b) by 791 days.

This patent is subject to a terminal disclaimer.

(21) Appl. No.: 09/751,774

(22) Filed: Dec. 29, 2000

(65) Prior Publication Data

US 2002/0087090 A1    Jul. 4, 2002

(51) Int. Cl.
*A61B 5/402* (2006.01)

(52) U.S. Cl. .................. 600/522; 600/523; 607/60; 709/218

(58) Field of Classification Search ............ 600/510, 600/522; 709/217–219; 607/60
See application file for complete search history.

(56) References Cited

U.S. PATENT DOCUMENTS

| | | | |
|---|---|---|---|
| 4,489,387 A * | 12/1984 | Lamb et al. ............... 709/237 |
| 4,791,936 A * | 12/1988 | Snell et al. ............... 600/510 |
| 4,890,623 A | 1/1990 | Cook et al. ............... 128/642 |
| 5,297,549 A | 3/1994 | Beatty et al. ............. 128/642 |
| 5,392,400 A * | 2/1995 | Berkowitz et al. ........ 709/203 |
| 5,427,112 A | 6/1995 | Noren et al. ............. 128/702 |
| 5,553,611 A | 9/1996 | Budd et al. .............. 128/642 |
| 5,566,096 A | 10/1996 | Wodlinger et al. ........ 364/574 |
| 5,640,967 A | 6/1997 | Fine et al. ............... 128/710 |
| 5,662,108 A | 9/1997 | Budd et al. .............. 128/642 |
| 5,706,823 A | 1/1998 | Wodlinger ............... 128/696 |
| 5,740,370 A * | 4/1998 | Battersby et al. ......... 709/219 |
| 5,743,859 A | 4/1998 | Wodlinger et al. ........ 600/522 |
| 5,813,991 A | 9/1998 | Willis et al. ............. 600/510 |
| 5,847,198 A | 12/1998 | Chambers et al. ........ 560/192 |
| 6,035,328 A * | 3/2000 | Soukal .................... 709/217 |
| 6,304,788 B1 * | 10/2001 | Eady et al. .............. 600/300 |
| 6,575,901 B1 * | 6/2003 | Stoycos et al. ........... 600/300 |

* cited by examiner

*Primary Examiner*—Andrew M. Dolinar
(74) *Attorney, Agent, or Firm*—Fletcher Yoder

(57) ABSTRACT

A distributed multi-user system for real time data access during cardiology procedures. The system includes an interactive computer network which can be used to simultaneously display data from a cardiology procedure on a plurality of devices and at a plurality of locations. The system is implemented through various replication topologies which allow the simultaneous access a cardiology study during the procedure. The study can be displayed at any of the plurality of locations, which may be local or remote, during the procedure.

22 Claims, 5 Drawing Sheets

DISTRIBUTED MULTI-USER REPLICATION-BASED SYSTEM FOR REAL TIME DATA ACCESS DURING CARDIOLOGY PROCEDURES

BACKGROUND OF THE INVENTION

1. Field of the Invention

The present invention relates generally to a distributed multi-user system for real time data access during cardiology procedures and, more particularly, to an interactive computer network which can be used to simultaneously display and manipulate data from a cardiology procedure on a plurality of devices and at a plurality of locations during the cardiology procedure.

2. Background of the Related Art

State of the art test and treatment facilities are essential to providing accurate monitoring, diagnoses, and treatment of heart disease. Medical facilities are often equipped to monitor and diagnose both mechanical and electrical defects in the heart. The present invention relates to the monitoring of the heart's electrical activity.

The heart is a muscle and, like other muscles, it contracts when it is electrically stimulated. Unlike other muscles, however, the heart has its own electrical system which can generate electrical impulses to stimulate the contraction of the muscle and thus keep the heart beating in rhythmic sequence so the blood is continually pumped throughout the body.

An electrophysiology study (EPS) is an invasive test involving the monitoring of the electrical signals in the heart. When defects in the heart tissue interfere with the normal formation or conduction of the heart's electrical activity, abnormal heart rhythms, known as cardiac arrhythmias, may develop. Cardiac arrhythmias may be caused by congenital defects, tissue damage due to heart attacks, or diseases such as arteriosclerosis (the deposition of fatty substances in the inner layer of the arteries) for instance, which accelerate, delay, or redirect the transmission of electrical activity, thereby disrupting the normal rhythmic contractions of the chambers of the heart. The electrophysiology study is used to assist in evaluating cardiac arrhythmias.

The basic electrophysiology procedure involves the recording and pacing of electrical signals within localized areas of the heart. During this study, catheters are placed near critical areas of the heart to record the heart's electrical signals. The heart is paced in various ways to study the speed and location of the flow of electricity within the heart. Typically, the study is used to determine if the heart has a tendency to pump faster or slower than normal and if the rhythm is dangerously irregular and thus requires treatment. Therapies for various rhythm disorders include medication, catheter ablation of the pathway, pacemakers, and defibrillators.

Tachycardia is an arrhythmia characterized by an abnormally fast heart rate (more than one-hundred beats per minute). Tachycardia falls into two categories, ventricular tachycardia (VT) and supra-ventricular tachycardia (SVT). VT is tachycardia that originates in the ventricles of the heart. SVT originates in the atria or at the junction between the atria and the ventricles of the heart. VT is a potentially life-threatening condition caused by either abnormally rapid impulse formation or by slow ventricular conduction which interferes with the heart's normal electrical activity and causes abnormally frequent contractions in the ventricles. Rapid ventricular contractions often result in significantly reduced cardiac output due to the inefficient pumping of the blood from the heart. As a result, the body receives an inadequate supply of oxygen which may cause dizziness, unconsciousness, cardiac arrest, or death.

Patients suspected of suffering from VT are initially screened by a cardiologist (doctor specializing in the heart) by means of external cardiac monitoring, typically in the form of an electrocardiogram. An electocardiogram captures electrical activity from surface leads placed on the patient's chest for twenty-four hours. When further testing is warranted, the patient is referred to a cardiac electrophysiologist (cardiologist who specializes in the electrical functioning of the heart) for an EPS.

An EPS evaluates the electrical integrity of the heart by stimulating multiple intra-cardiac sites and recording the electrical response. During an EPS, a patient's clinical tachycardia is induced in a controlled setting to diagnose the tachycardia and select an appropriate treatment or combination of treatments. EP studies using currently available technology are often lengthy and tedious procedures which include probing the interior of two or more chambers of the heart with single point contact catheters causing significant discomfort for the patient. However, single point contact catheters have limited utility in diagnosing complex tachycardia. The limited data produced in point by point mapping often fails to provide the electrophysiologist with sufficient diagnostic power for a complete understanding of the tachycardia.

One form of treatment of VT and SVT type arrhythmias which is becoming increasingly popular is catheter ablation. During the ablation (or "elimination") procedure, which is similar to the procedure used in the EPS, a special catheter is inserted into the patient to deliver energy, such as radio frequency (RF) energy, to the precise areas of the heart which have been identified to cause the abnormal heartbeat. The tip of the catheter heats up and destroys the surrounding tissue thereby correcting the anomalous circuit within the heart which is causing the abnormal electrical activity. Catheter ablation is a potentially curative treatment which is continually being developed.

To perform procedures such as the EPS or catheter ablation, a cardiac catheterization lab is provided in which multiple clinicians can diagnose and treat heart conditions. These clinicians need to interact with, manipulate, and document observations on the clinical data in the study record. It would be advantageous for clinicians to be able to interact with and manipulate the clinical data simultaneously during a EP procedure. Such clinicians may include a primary physician, nurse, anesthesiologist, cardiovascular technician, radiology technician, consulting physician, and so forth. For example, it may be necessary for a cardiovascular technician, a primary physician, and a nurse to view the same information simultaneously during an EP procedure. However, each clinician may be located in a different part of the cardiac catheterization lab. Further, consulting physicians who may be located remotely may need to view the same clinical data during an EP procedure to provide real-time consultation on a particular procedure. Current techniques to accommodate the complex workflow in a cardiac catheterization lab are insufficient to meet these needs. Up to 128 channels of data may need to be recorded at a rate of 1K-byte/sec making the acquisition, displaying and manipulation of such data difficult to manage.

Prior techniques which have been employed in cardiac catheterization labs may not permit viewing of an EPS in real time on a system other than the acquisition station during the procedure, nor do they provide the capability of providing simultaneous access by different clinicians. FAX machines are currently used to employ the help of a consulting physician at a remote location. During an EPS, certain data and diagrams may be printed. These pages may then be delivered to a remote location via facsimile. Disadvantageously, this process is slow and tedious. The time it takes to exchange information between clinicians using the current techniques may be critical during an EPS. Further, the lack of simultaneous viewing capability of an EPS which is currently being conducted may result in critical delays in diagnoses and treatment of heart anomalies.

The present technique may address one or more of the problems set forth above.

SUMMARY OF THE INVENTION

The present technique describes a distributed multi-user system for real time data access during cardiology procedures. The system includes an interactive computer network which can be used to simultaneously display data from a cardiology procedure on a plurality of devices and at a plurality of locations. The system is implemented through various replication topologies which allow the simultaneous access of a cardiology study during the procedure. The study can be displayed at any of the plurality of locations, which may be local or remote, during the procedure. Any updates to the data during the procedure will be distributed to the plurality of locations for real-time viewing of the updated data.

DETAILED DESCRIPTION OF THE INVENTION

Figure 1:
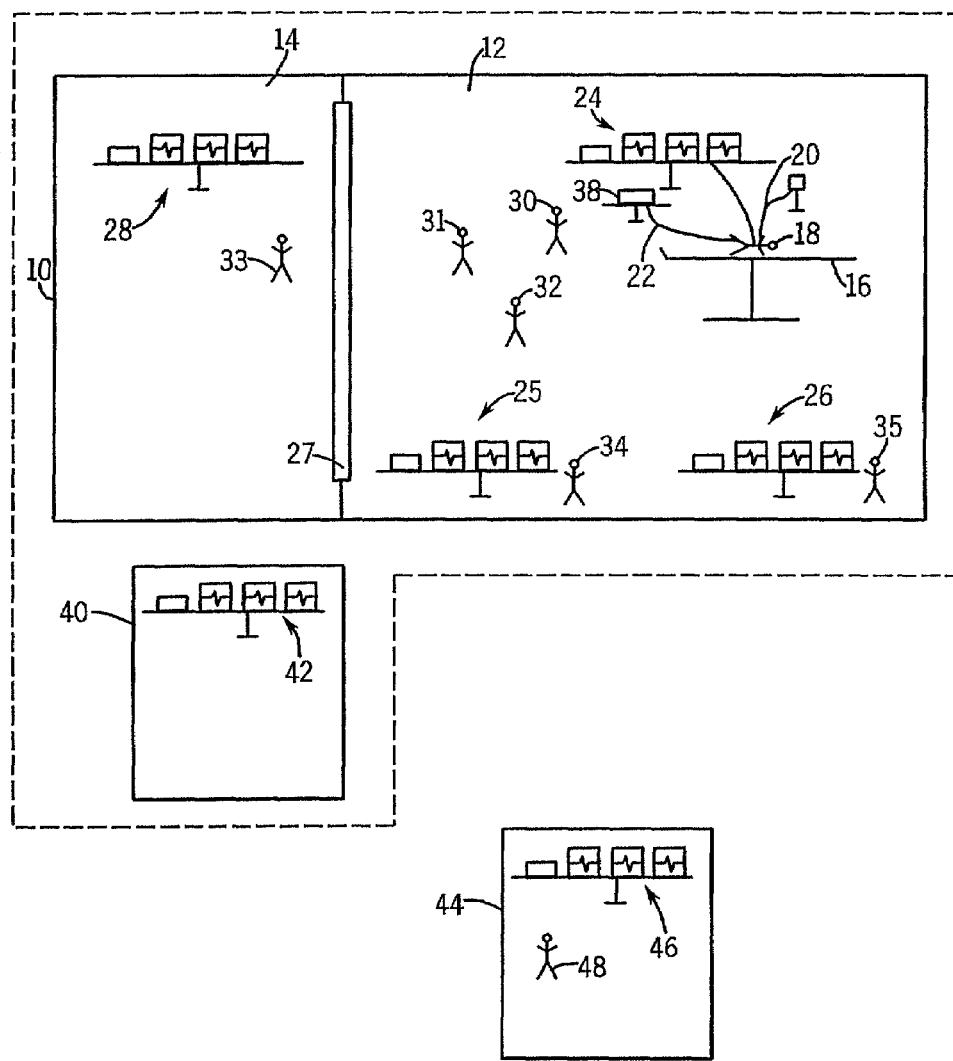
FIG. 1 is a block diagram of an exemplary system including a cardiac catheterization lab and local and remote client workstations.

As previously discussed, a cardiac catheterization lab may be used by multiple clinicians to perform procedures such as an EPS or catheter ablation. FIG. 1 illustrates one embodiment of a catheterization lab 10. The catheterization lab 10 generally includes a procedure room 12 and a control room 14. The procedure room 12 is generally the room in which the physical catheterization procedure takes place. The control room 14 is generally the room in which the control of the data gathering and display takes place. The procedure room 12 may include a bed 16 in which a patient 18 is placed during a cardiac catheterization procedure such as an EPS procedure or catheter ablation. An intravenous (IV) line 20 may be placed in the arm of the patient 18 to provide a means of dispensing medication during the procedure. Catheters 22 may be inserted through the femoral vein in the groin of the patient 18. An x-ray imaging system (not shown) may be used to guide the catheter 22 into the appropriate region of the patient's heart. The patient 18 is also connected to an acquisition workstation 24 to receive the data taken during the study and which include display monitors to provide imaging data during the procedure. Further, the lab 10 may also include one or more workstations 25 and 26 with display monitors to provide additional support during a procedure, as discussed below.

The catheterization lab 10 may also include a glass partition 27, such as lead glass which separates the procedure room 12 from the control room 14. The control room 14 also includes a workstation 28 with display monitors which may be similar to the display monitors contained in the procedure room 12.

A team of clinicians generally conducts an EPS procedure. The team may include a doctor 30 to perform the procedure, a nurse 31 to maintain the patient's vital signs, a scrub nurse 32 to assist the doctor 30 with the procedure, a monitoring technician 33 who is responsible for providing the doctor 30 with the information and data that the doctor 30 needs to see during the procedure, and other clinicians 34 and 35 who assist in monitoring and/or annotation of a particular procedure, for example. The monitoring technician 33 is generally stationed in the control room 14. The monitoring technician 33 is in communication with the doctor 30 during the EPS procedure through an intercom system, for example, and provides information in response to requests from the doctor 30 while the procedure is being conducted.

During the procedure, the doctor 30 stimulates the patient's heart with small electrical signals delivered through the catheter 22 to make the heart beat at various rates. The electrical signals are delivered from a stimulator 38 which may be a separate device from the acquisition workstation 24. Because the monitoring technician 33 responds to requests from the doctor 30 to control the data viewed on the display monitors associated with the acquisition workstation 24 in the procedure room 12, the display monitors associated with the workstation 28 in the control room 14 preferably display identical information. Likewise, other display monitors, such as those associated with workstations 25 and 26, preferably display the information gathered during the procedure. Further, workstations including display monitors may advantageously be installed in other areas within the same facility but outside the catheterization lab 10, such as a local diagnosis area 40. The local diagnosis area 40 may include a workstation 42 with display monitors from which to view a study during or after a procedure.

Similarly, a facility 44 which may be located remotely with respect to the lab 10, may include a workstation 46 with display monitors to be used by a remote specialist 48. The remote specialist 48 may participate during the procedure to provide critical insight into the study which may not be available through the clinicians available locally. For instance, a remote specialist 48 whose office facility is equipped with display monitors associated with workstation 46, can observe a procedure being performed in the catheterization lab 10 without being present during the procedure. As the remote specialist 48 observes the study, he can advise the local clinicians in real time while the procedure is being performed.

To optimize the treatment of the patient 18, it may be desirable to provide each set of display monitors associated with workstations 24, 25, 26, 28, 42 and 46 with identical information simultaneously during the procedure. Further, it may be desirable to provide updates to each workstation in real time. In one embodiment of the present technique, a plurality of local areas and remote areas will advantageously include display monitors which will allow real-time updating of the images in response to changes implemented during the procedure. The technique employed by the present embodiment is a dynamic technique which provides interactive reviewing of the EPS during the procedure. While a prior technique allowed only end of study transfers, the present technique provides for the transfer of information during the EPS study.

Figure 2:
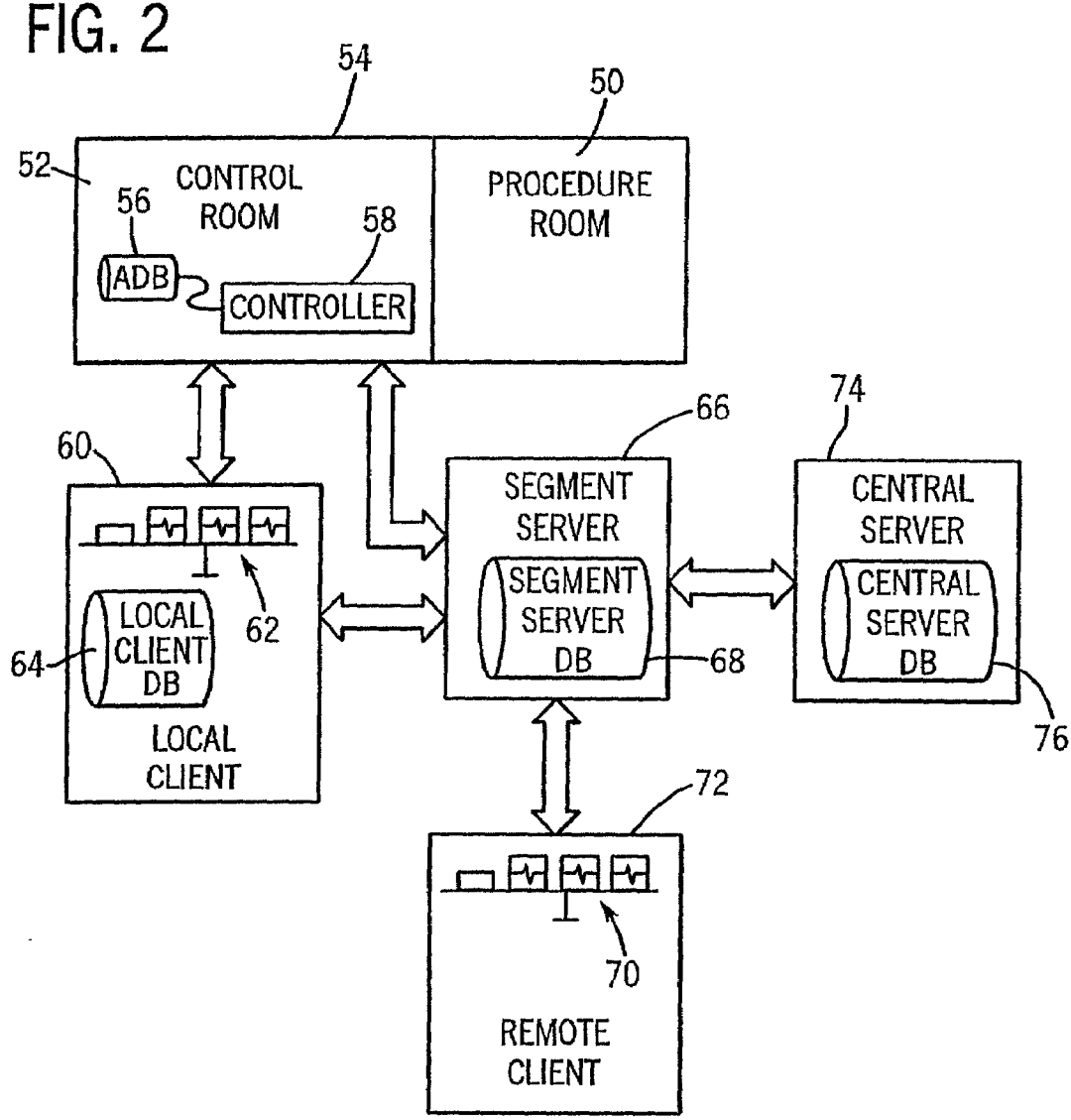
FIG. 2 is a block diagram illustrating an exemplary implementation of the present technique.

A general block diagram of the present scheme is indicated in FIG. 2. For simplicity new reference numerals are used to describe FIG. 2. However, it should be evident that some of the elements in FIG. 2 were previously described in FIG. 1 using different reference numerals. A more detailed description of specific embodiments of the present scheme are described herein with reference to FIGS. 3–5.

Referring initially to FIG. 2, a cardiac catheterization lab comprising a procedure room 50 and a control room 52 is generally illustrated by block 54. As previously discussed, the lab 54 facilitates the acquisition of data received during an EPS procedure. An acquisition database 56 and a controller 58 may reside in the control room 52 to store data taken during a procedure. The data is initially taken from a patient (not shown in FIG. 2) in the procedure room 50 and delivered to the control room 52 via a local area network, for instance, to be stored in the acquisition database 56.

In one implementation of the present technique, the controller 58 in the control room 52 serves as the "publisher" to a "local client" 60. A "local client" refers to any user workstation located proximate to the control room 52, such as those workstations within the procedure room 50 or within a hospital in which the lab 54 is housed. The "publisher" is responsible for the real-time processing of the data. Local clients, such as local client 60, can access the acquisition database 56 directly from a user workstation 62 during the EPS procedure without going through a client server. In this topology, the local client 60 is coupled to the lab 40 via a local area network, for example. The local client 60 can communicate directly with the controller 58, and can exchange data with the acquisition database 56. The controller 58 will "publish" the EPS data to the requesting workstation 62.

Each local client 60 may also include a local client database 64 in which to store study data. Each time the data is updated during the procedure, which may be continuous, the data is sent to the publisher (controller 58) for dissemination in real or near-real time (0–30 sec. from update). The controller 58 then replicates the study and distributes it to any local client, such as local client 60, who may be viewing the particular study. This provides a real time means of displaying updates during an EPS procedure for local clients, such as local client 60.

As discussed above, to facilitate the updating of studies the publisher, controller 58 manages the updates and the dataflow. Each time a study is changed, the information is fed to the acquisition database 56. The data is then replicated and sent to all other subscribers who are currently viewing the present study. One typical mechanism for implementing this and other topologies is by implementing a merge replication architecture.

Merge replication can be viewed as a mechanism for implementing the present embodiments. Prior techniques of decentralizing study data by publishing from a central location, such as a server, to multiple remote locations residing within the cardiac catheterization labs or throughout a medical institution only provide for the instances when all data is entered at the central sites. Conversely, the present technique of using merge replication allows the system to utilize the present topology in a modified way. In this topology, a subscriber can process a transaction and have it propagated to the publisher. This replication topology functions significantly different from prior systems. As can be appreciated by one skilled in the art, merge replication is the most robust and manageable replication topology used in the industry. The replication procedure can be implemented using commercially available software, such as applications available commercially from Microsoft Corporation of Redmond, Washington or Oracle Corporation of Redwood City, California, for example.

Advantageously, by serving as the publisher for local clients, the controller 58 ensures that failure in the server operation will not disable the use of the study for local clients. Regardless of whether a server which may be associated with the acquisition database 56 is functioning, local clients will be able to access the acquisition database 56 and will be able to view and annotate any EPS being conducted.

However, in certain instances, it may be desirable to have local clients receive study data through a server. A second topology generally includes a segment server 66 and a segment server database 68, as illustrated in FIG. 2. The segment server 66 may be responsible for coordinating and universally updating changes made during an EPS procedure regardless of where the updates are being delivered. Each time a change to an EPS is made, the data is sent from the controller 58 to the segment server 66 and stored in the segment server database 68. The segment server 66 delivers a message to all clients currently subscribing to the system indicating that a change to the study has been made and that the data should be refreshed. This process may actually be invisible to a user and the client system may automatically update the study when the segment server 66 indicates that changes have been made. Each local client 60 having a user workstation 62 and any remote client 72 having a user workstation 70 that has the current EPS open receives the updated information from the segment server 66. This procedure is accomplished by replicating the segment server database 68 upon synchronization of the clinical data from the control room 52.

In this topology, the "publisher" is the controller 58 generally residing in the control room 52. The "subscriber" is generally the segment server 66 and the segment server database 68. It should be understood however that the subscriber may also perform as a publisher if the data in the EPS study is edited and a client, such as a local client 60 or a remote client 72, is working through the segment server 66. For example, certain parameters may be entered at a nurses station. This data advantageously flows back, in real-time, to all other local clients 60 and remote clients 72 viewing that particular study. The segment server 66, thus, subscribes to the updates from the controller 58 and then publishes the updated study to the local and remote clients 60 and 72. Thus, in this topology, the data is transmitted from the control room 52 to a segment server 66. The segment server 66 ultimately serves as the central publisher. The acquisition database 56 as well as subscriber workstations (located at facilities of the local and remote clients 60 and 72) replicate their data to a single segment server 66 which distributes the updated data to any subscribers viewing the current EPS procedure.

It may be advantageous to provide a central server 74, including a central server database 76, coupled to the segment server 66. As the number of clients and cardiac catheterization labs which provide data to the segment server 66 increases, it may be advantageous to periodically transfer data from the segment server database 68 to a central server database 76 for permanent storage.

Figure 3:
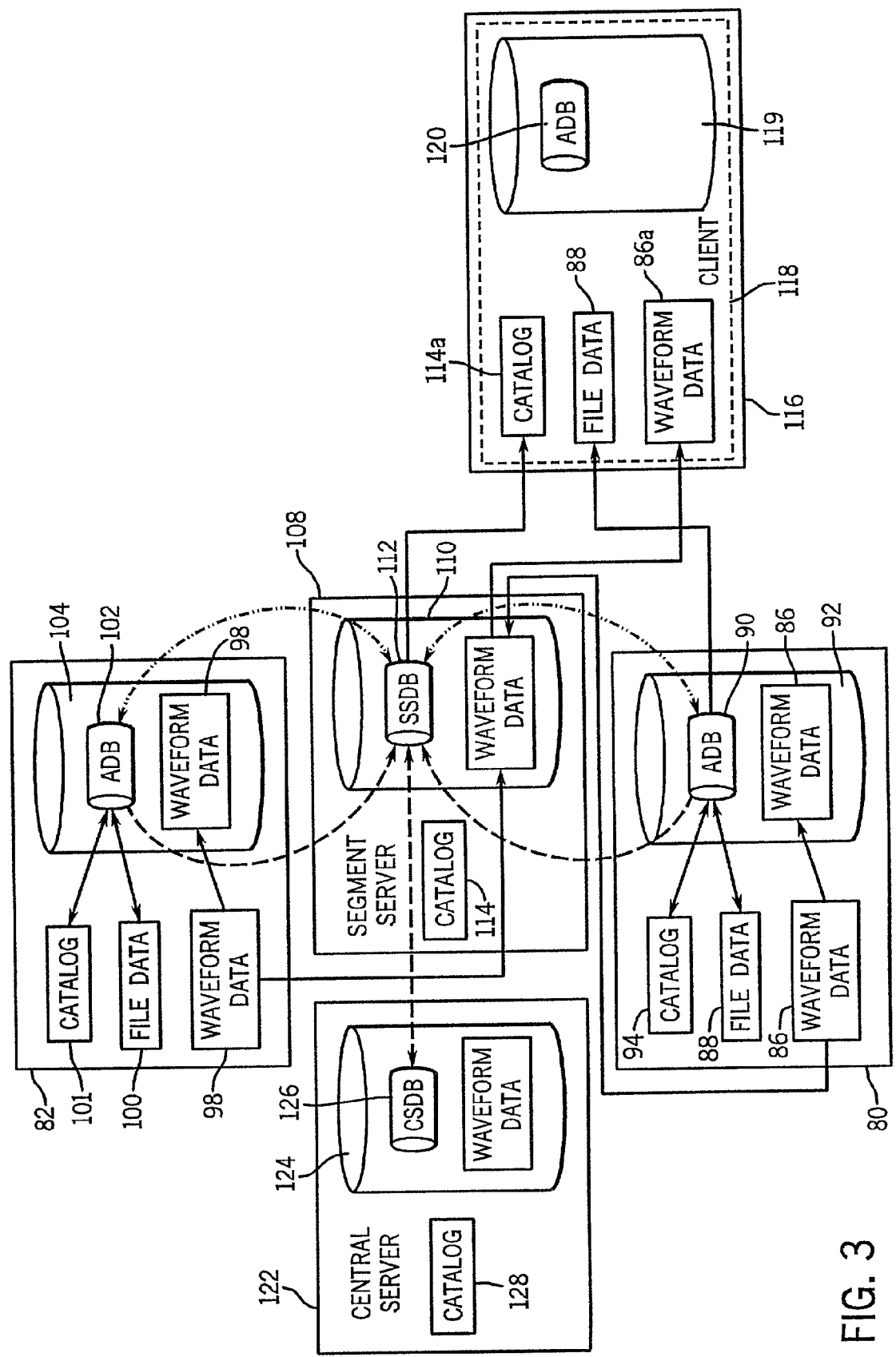
FIG. 3 is a block diagram illustrating a more detailed embodiment of an exemplary implementation of the present technique.

Generally, FIG. 3 illustrates a more detailed embodiment of one implementation of the present scheme, depicting the simultaneous acquisition of study data in two catheterization labs. Up to this point and to simplify the general description, references to study data have been presented as a unified set of information which may be viewed and annotated. However, it may be advantageous to divide the study data into different types of data. In a present implementation, study data may be comprised of two data types: waveform data and file data. The advantages of separating data types will become evident in the description of FIG. 3, below.

Specifically, FIG. 3 illustrates two acquisition workstations 80 and 82. The acquisition workstations 80 and 82 may be located in the same catheterization lab or in two different catheterization labs. The acquisition workstations 80 and 82 are used to acquire and store study data taken during an EPS. The acquisition workstation 80 collects both types of study data, waveform data 86 and file data 88. The waveform data 86 comprises the graphical illustrations and information taken during the study. The file data 88 comprises the text accompanying the waveform data 86, as well as any annotations made by clinicians or clients. The file data 88 is stored in an acquisition database 90, which may be included in an acquisition storage unit 92, such as a hard drive. The waveform data 86 is stored in the acquisition storage unit 92. For each set of file data 88, a pointer is maintained in the acquisition database 90 to provide the corresponding waveform file path. The catalog 94 in the acquisition workstation 80 is a file that lists the studies located on that particular acquisition workstation 80.

Similarly, the acquisition workstation 82 collects both waveform data 98 and file data 100. The file data 100 is stored in an acquisition database 102, which may be included in an acquisition storage unit 104. The waveform data 98 is stored in the acquisition storage unit 104. For each set of file data 100, a pointer is maintained in the acquisition database 102 to provide the corresponding waveform file path. The catalog 106 in the acquisition workstation 82 is a file that lists the studies located in the acquisition workstation 82.

Each acquisition workstation 80 and 82 is coupled to a segment server 108. The segment server 108 includes a segment server storage unit 110 which may comprise a segment server database 112. Aside from storing waveform data 86 and 98 in their respective acquisition storage units (92 and 104), the acquisition workstation 80 and 82 stores the waveform data 86 and 98 in the segment server storage unit 110. The waveform data 86 and 98 is written to the segment server 108 via a low priority background thread. If the connection between the segment server 108 and one of the acquisition workstations 80 and 82 is interrupted, the acquisition workstations 80 and 82 are not compromised. Finally, the segment server catalog 114 is a file that lists the studies on all acquisition workstations which are attached to the segment server 108 (here acquisition workstations 80 and 82) and identifies on which workstation each study resides. The segment server catalog 114 is updated by replication of selected database information from each acquisition database (90 and 102).

A local client, such as local client 116, may wish to view the study record which is currently being produced by the workstation 84. The local client has a workstation 118 and a client storage unit 119, including a local client database 120. The local client 116 may concurrently review and edit study data by selecting a particular study from the replicated copy of the segment server catalog 114 which may be accessed from the local client 116. The segment server catalog 114 lists all of the studies from any of the acquisition stations which are linked to the segment server 108. A non-annotatable copy of the segment server catalog 114 which is accessed by the local workstation 116 is generally illustrated by reference numeral 114a. The application stored on the client workstation 118 is then redirected by the file path stored in the segment server catalog 114 to the acquisition database 90. The local client 116 is then essentially linked to the file data 88 stored in the acquisition database 90 by a link such as a local area network. The local client 116 receives the file data 88 directly from the acquisition database 90. The local client may view and annotate any of the file data 88 on the local client workstation 118. The file data 88 is returned to the acquisition database 90 with any annotations stored in the file.

While the file data 88 residing in the acquisition database 90 can generally be accessed and annotated directly by a local client 116, the waveform data 86 is not directly accessible by the local client 116. Instead, the local client 116 receives the replicated waveform data 86a from the segment server 108. One reason for this particular scheme is to prevent a local client 116 from altering the waveform data 86. Since the waveform data is a representation of the raw test results from an EPS study, it may be important to safeguard the integrity of the data by providing access to only the replicated waveform data 86a as described in the present embodiment.

Finally, it may be advantageous to provide a central server 122 to permanently store (archive) study data once a study has been completed. The central server 122 may include a central server storage unit 124 to store waveform data and a central server database 126 to store file data. Further, the central server 122 may include a central server catalog 128 which lists the studies on all segment servers, such as segment server 108, which are coupled to the central server 122. Since each segment server 108 includes a catalog 114 listing all study records contained on any of the acquisition workstations which are coupled to the segment server 108, such as acquisition workstations 80 and 82, the central server catalog 128 provides a path to any study contained on any of the acquisition workstations throughout the network. The archival scheme is further discussed with reference to FIG. 4.

Figure 4:
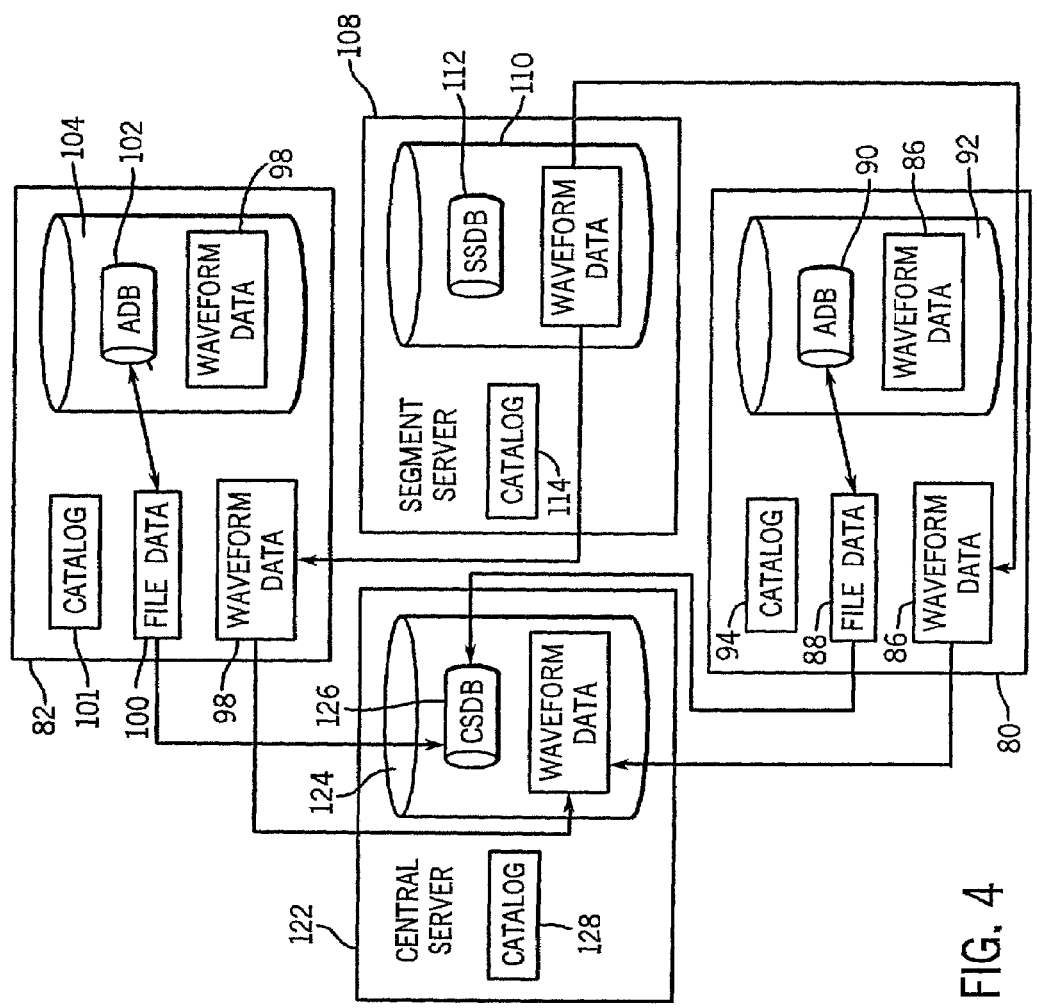
FIG. 4 is a block diagram illustrating an archival scheme for permanently storing study data in accordance with the present technique.

FIG. 4 illustrates one embodiment of an archival scheme for permanently storing study data once a study is complete. The Archival Generator (AG) software application selects study data older than a user selected number of days from short-term storage in an acquisition database 90 and 102. All selected study records in the acquisition database 90 and 102, including both the file data 88 and 100 and the waveform data 86 and 98, are copied to the central server 122. Once copied, the data may be tested for data integrity by comparing the study record to the study record stored in the segment server 108. Once integrity is verified, the study records can be deleted from the acquisition databases 90 and 102, as well as the segment server database 108. The central server catalog 128, the segment server catalog 114 and the acquisition station catalogs 94 and 101 are updated appropriately.

Figure 5:
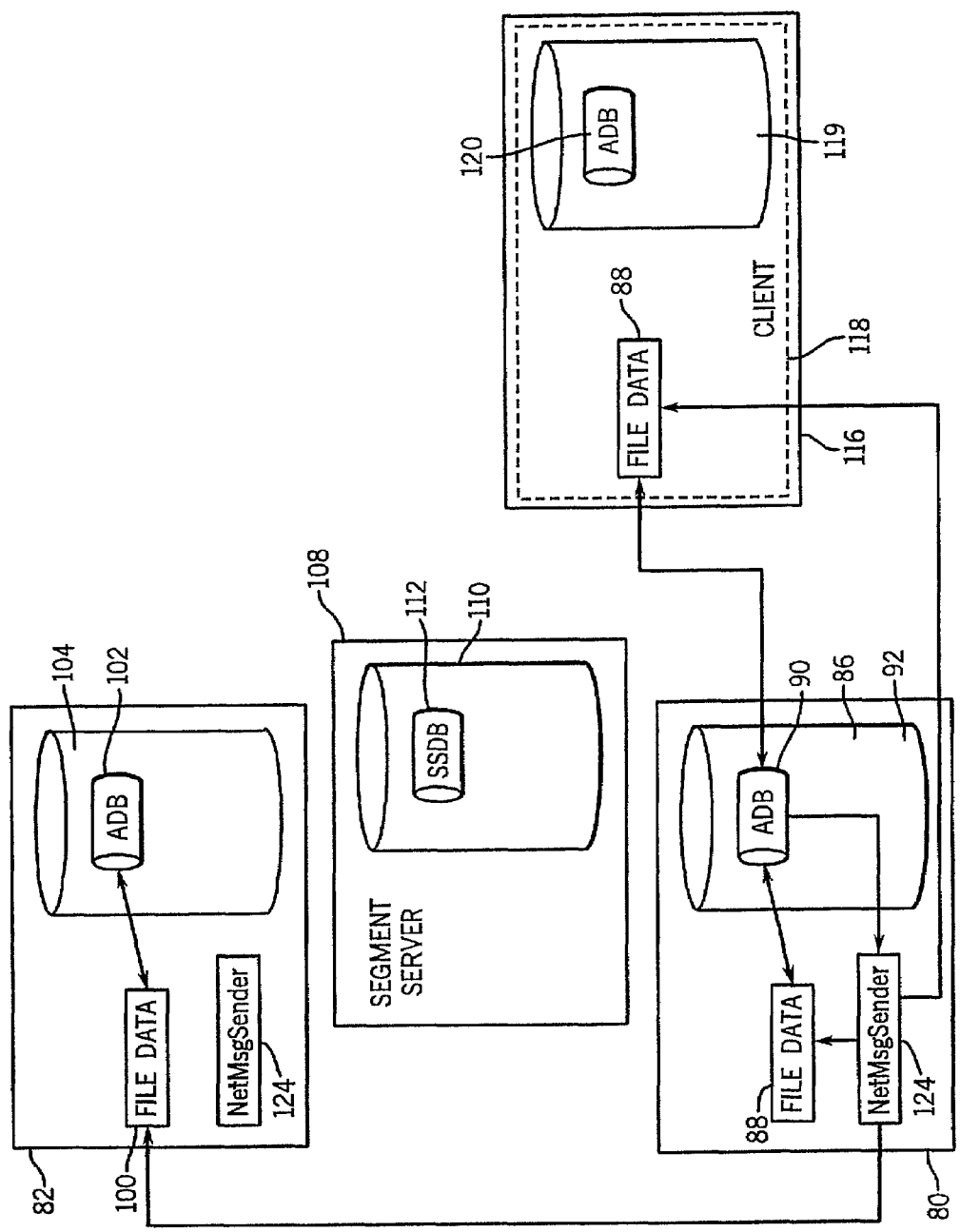
FIG. 5 is a block diagram illustrating a messaging technique in accordance with the present technique.

It should be evident that to provide real-time updates of the study data while a client is reviewing a study which is currently being conducted, a messaging system may be implemented to insure that updates are sent to clients viewing the particular study. FIG. 5 illustrates one implementation of a messaging technique corresponding to the present system. When the file data 88 is inserted into the acquisition database 90, a message record may be added to a socket table in the acquisition database 90. A messaging application, such as NetMsgSender, sends all message records located in the socket table through an output port of the acquisition workstation 80, such as TCP/IP Port 50,000, to all systems, such as local workstation 118, which are configured to receive data from the acquisition workstation 80. The message records may be sent at a user-configurable interval. All acquisition workstations 80 and 82 listen on the output port. If a message is received on a particular workstation, such as workstation 80, the workstation 80 reads the message and determines whether the message pertains to an active study. If it does, the workstation 80 determines which event is affected and if the message is an update, insert or delete the appropriate study data. The data is then refreshed on the local client workstation 118.

While the present embodiment discloses a technique using data taken during an EPS, it should be evident to one skilled in the art that the technique described herein can be applied to other cardiology procedures performed in a catheterization lab in which electrical and/or hemodynamic data may be obtained.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of accessing a study record taken during a cardiac catheterization procedure, the procedure being conducted in a cardiac catheterization lab, comprising the acts of
   (a) inserting at least one catheter into a patient comprising a heart, the catheters terminating in a position proximate to the heart and comprising one or more sensors configured to sense data from the heart;
   (b) stimulating the heart with electrical signals from the catheter;
   (c) sensing data from the heart;
   (d) transmitting the data from the sensors to a data collection device;
   (e) transmitting the data from the data collection device to a central publisher;
   (f) replicating the data;
   (g) transmitting the replicated data from the central publisher to a plurality of client workstations; and
   (h) simultaneously displaying the data on the plurality of client workstations during the cardiac catheterization procedure.

2. The method, as set forth in claim 1, wherein the catheterization procedure comprises a electrophysiology procedure.

3. The method, as set forth in claim 1, wherein the catheterization procedure comprises an ablation procedure.

4. The method, as set forth in claim 1, wherein the central publisher comprises a server.

5. The method, as set forth in claim 4, wherein the server is located locally with respect to the cardiac catheterization lab.

6. The method, as set forth in claim 1, wherein the central publisher is located within the cardiac catheterization lab.

7. The method, as set forth in claim 1, wherein each of the plurality of client workstations comprises a display monitor.

8. The method, as set forth in claim 1, wherein act (c) comprises the act of sensing electrical data from the heart.

9. The method, as set forth in claim 1, wherein act (c) comprises the act of sensing hemodynamic data from the heart.

10. The method, as set forth in claim 1, wherein act (h) comprises simultaneously displaying the data on a plurality of client systems during the procedure, wherein at least one of the plurality of client workstations is located remotely with respect to the cardiac catheterization lab.

11. The method, as set forth in claim 1, wherein act (h) occurs in real time.

12. A method of accessing a study record taken during a cardiac catheterization procedure, the procedure being conducted in a cardiac catheterization lab, comprising the acts of:
   (a) transmitting data from a catheter to a data collection device;
   (b) transmitting the data from the data collection device to a central publisher;
   (c) replicating the data;
   (d) transmitting the replicated data from the central publisher to a plurality of client workstations; and
   (e) simultaneously displaying the data on the plurality of client workstations during the cardiac catheterization procedure.

13. The method, as set forth in claim 12, wherein the catheterization procedure comprises a electrophysiology procedure.

14. The method, as set forth in claim 12, wherein the catheterization procedure comprises an ablation procedure.

15. The method, as set forth in claim 12, wherein the central publisher comprises a server.

16. The method, as set forth in claim 15, wherein the server is located locally with respect to the cardiac catheterization lab.

17. The method, as set forth in claim 12, wherein the central publisher is located within the cardiac catheterization lab.

18. The method, as set forth in claim 12, wherein each of the plurality of client workstations comprises a display monitor.

19. The method, as set forth in claim 12, wherein act (a) comprises the act of transmitting electrical data.

20. The method, as set forth in claim 12, wherein act (a) comprises the act of transmitting hemodynamic data.

21. The method, as set forth in claim 12, wherein act (e) comprises simultaneously displaying the data on a plurality of client workstations during the procedure, wherein at least one of the plurality of client workstations is located remotely with respect to the cardiac catheterization lab.

22. The method, as set forth in claim 12, wherein act (e) occurs in real time.

* * * * *